United States Patent [19]

Kifune

[11] Patent Number: 4,704,268

[45] Date of Patent: Nov. 3, 1987

[54] METHOD FOR MANUFACTURE OF BIODEGRADABLE DRUG DONOR AND DRUG DONOR MADE THEREBY

[75] Inventor: Koji Kifune, Nara, Japan

[73] Assignee: Unitika Ltd., Hyogo, Japan

[21] Appl. No.: 637,191

[22] Filed: Aug. 2, 1984

[30] Foreign Application Priority Data

Aug. 8, 1983 [JP] Japan ................................. 58-145428

[51] Int. Cl.$^4$ ........................... A61K 9/00; A61K 9/22
[52] U.S. Cl. ..................................................... 424/488
[58] Field of Search ..................................... 424/16, 19

[56] References Cited

U.S. PATENT DOCUMENTS

| | | | |
|---|---|---|---|
| 3,911,098 | 10/1975 | Capozza | 424/19 |
| 3,989,535 | 10/1975 | Capozza | 424/19 |
| 4,029,727 | 6/1977 | Austin et al. | 424/19 |
| 4,059,457 | 11/1977 | Austin | 424/19 |

FOREIGN PATENT DOCUMENTS 57-134412 8/1982 Japan .

OTHER PUBLICATIONS

R. A. A. Mozzarelli *Chitin*, pp. 58–65, Pergamon Press (1977).
Filar and Wirick, "Bulk and Solution Properties of Chitosan", *Proceedings of the First International Conference on Chitin/Chitosan*, (Mozzarelli and Pauser Eds. 1978), U.S. Department of Commerce, National Technical Information Service, PB-285640.

*Primary Examiner*—Stanley J. Friedman
*Attorney, Agent, or Firm*—Sughrue, Mion, Zinn, Macpeak & Seas

[57] ABSTRACT

A method for the manufacture of a biodegradable drug donor capable of gradually releasing a drug to a living body and the drug donor made thereby are described, said method comprising dissolving a chitin in a solvent to thereby prepare a dope, bringing said dope into contact with a liquid coagulant to thereby form a swelled mass containing said chitin, impregnating said chitin-containing swelled mass with a solution containing a drug, and subsequently drying the impregnated swelled mass.

24 Claims, No Drawings

METHOD FOR MANUFACTURE OF BIODEGRADABLE DRUG DONOR AND DRUG DONOR MADE THEREBY

FIELD OF THE INVENTION

This invention relates to a method for the manufacture of a donor capable of providing controlled release of a drug and a drug donor made thereby. More particularly, this invention relates to a method for the manufacture of a donor having a drug dispersed in chitin (poly-N-acetyl-D-glucosamine) which is decomposable and assimilable within the living body, with the donor being such that the donor, upon contact with a body fluid, releases the drug little by little into the body fluid over a long period of time, and the donor itself is finally disintegrated and eliminated, with the time of the release of the drug being thus controlled.

BACKGROUND OF THE INVENTION

A number of methods have been heretofore proposed for the purpose of providing prolonged release of a drug within a living body, particularly at a prescribed internal region. Ideally, the donor is desired to be wholly disintegrated and eliminated after completion of the action of donation. For this purpose, the housing part of the donor should be biodegradable.

A drug release device making use of this principle is disclosed in U.S. Pat. No. 3,911,098, corresponding to Japanese Patent Application (OPI) No. 123815/75 (The term "OPI" as used herein refers to a "published unexamined Japanese patent application".). The method for the manufacture of this drug release device comprises intimately mixing a given drug with a chitin solution and molding the resultant blend in a given shape, to thereby provide a release device. This method, however, is practicable only with a derivative of chitin which is soluble in water. Other chitins and chitin derivatives which are not soluble in water suffer from a disadvantage that since most solvents of chitins are highly reactive, drugs which are bioactive components are often chemically degraded and deactivated. As examples of solvents for chitins, trichloroacetic acid, dichloroacetic acid, N-methyl pyrrolidone, and hexafluoroisopropyl alcohol have been known to the art. To ensure intimate blending of a drug and a chitin, the practice of first dissolving the chitin in a solvent as described above and subsequently dispersing the drug in the resultant solution has been followed. This practice has a disadvantage that during the course of the dispersion, the drug is liable to lose activity and the device consequently obtained is deficient in efficacy.

The inventors have conducted studies with a view to providing a biodegradable drug donor improved so as to overcome the drawbacks suffered by the conventional device as described above. It has consequently been found that a donor formed by wrapping a given drug with a film of chitin protects the drug against loss of activity and enables the drug to be gradually and substantially uniformly released to the living body. Such is described in Japanese Patent Application (OPI) No. 134412/82. However, when this donor makes use of hollow fibers, for example, the method for the manufacture thereof proves to be rather complicated because the drug and the film of chitin are two separate substances, and therefore must be prepared separately from each other and subsequently combined. Therefore, the development of a method which permits a drug donor of such advantageous behavior to be easily produced would be very desirable.

SUMMARY OF THE INVENTION

This invention relates to a method for the manufacture of a biodegradable drug donor capable of gradually releasing a drug to a living body and a drug donor made thereby, said method comprising dissolving a chitin in a solvent to thereby prepare a dope, exposing the dope to a liquid coagulant to thereby form a swelled mass containing the chitin, impregnating the chitin-containing swelled mass with a solution containing a drug, and subsequently drying the impregnated swelled mass.

DETAILED DESCRIPTION OF THE INVENTION

The term "chitin" as used in this invention means poly-(N-acetyl-D-glucosamine) obtained by treating crustaceans and insects with hydrochloric and caustic soda and refining the resultant solution by separation of proteins and calcium, and derivatives of the polymer. Examples of the derivative of chitin include deacetylation products (inclusive of chitosan), etherification products, esterification products, carboxymethylation products, hydroxyethylation products, and o-ethylation products of poly-(N-acetyl-D-glycosamine). Poly-[N-acetyl-6-o-(2'-hydroxyethyl)-D-glucosamine] and poly-[N-acetyl-6-o-(ethyl)-D-glucosamine] are specific examples.

Examples of the solvent used for dissolving chitin in the preparation of the dope of chitin in this invention include trichloroacetic acid, a mixture of trichloroacetic acid with a halogenated carbon compound (weight ratio: 20/80 to 80/20), dichloroacetic acid, a mixture of dichloroacetic acid with a halogenated carbon compound (weight ratio: 20/80 to 80/20), a mixture of N-methylpyrrolidone with lithium chloride (weight ratio: 90/10 to 95/5), a mixture of dimethylacetamide with lithium chloride (weight ratio: 90/10 to 95/5), trifluoroacetone, hexafluoroisopropyl alcohol, and an aqueous solution containing acetic acid.

In the present invention, the chitin is dissolved in such a solvent to prepare a dope, and this dope is brought into contact with a liquid coagulant to produce a swelled mass containing the chitin. In this case, the chitin-containing swelled mass is obtained in a desired shape, such as, for example, a bar, a sheet, or a thread.

To ensure production of the swelled mass in a uniform shape, a method may be adopted which comprises introducing the dope into a pressurized tank and extruding the dope through a desired die or a spinning nozzle by a metering pump such as, for example, a gear pump, into the liquid coagulant to be coagulated therein. In this case, as the coagulation proceeds, the liquid coagulant displaces the solvent in the dope and eventually gives rise to a swelled mass containing therein the liquid coagulant. Examples of the liquid coagulant desirably used for this purpose include water, alcohols such as methyl alcohol, ethyl alcohol, propyl alcohol, and butyl alcohol, and ketones such as acetone. In the present invention, the chitin-containing swelled mass formed as described above is immersed, with the liquid coagulant either left intact or replaced with some other liquid coagulant, in a solution containing the drug, and is left standing therein until the solution thoroughly displaces the liquid coagulant and the resultant wet mass is dried in a vacuum to expel the solvent and complete the drug donor. In this case, the liquid coagulant and the solvent for the solution of the drug must be selected from among substances which are incapable of impairing the activity of the drug.

The term "drug" as used in this invention means a substance which manifests a physiological activity in the biological environment, and, in this sense, embraces curative medicines to be used in humans and animals, preventive medicines, insecticides, insectifuges, and enzymes such as enzymes used in cosmetics and enzymes used for clinical tests.

Examples of the curative medicines and preventive medicines are as follows.

(1) Proteinaceous medicines such as insulin.
(2) Agents for combating infections such as antibiotics including penicillins, cephalosporins, polymyxin B, amphotericin, trichomycin, gramicidin S, colistin, nystatin, kanamycin, chloramphenicol, tetracycline, erythromycin, streptomycin, rifampicin, actinomycin, and chromomycin $A_3$.
(3) Cancer depressants such as carcinophilin, sarkomycin, bleomycin, mytomycine C, nitrogen mustard, nitrogen mustard-N-oxide, cyclophosphamide, merpheran, chlorambucyl, uracil mustard, triethylene melamine, triethylene thiophosphoamide, busulfan, pipobroman, carmustine, dacarbazine, procarbazine, dibromomannitol, dibromodarcitol, azathioprine, 6-mercaptopurin, thioguanine-thioisocin, 5-fluorouracil, 5-fluorodeoxyuridine, ftorafur, citracin arabinoside, cyclocytidine, 5-azacytidine, vincristine, vinblastine, podophyllofolic acid, 4-aminopterin, methotrexate, teropterin, dihydro-folic acid, tetrahydro-folic acid, 6-diazo-5-oxonolylleucin, azaserine, actinomycin C, D, chromomycin $A_3$, daunorubicin, L-asparaginase, adriamycin, and daunomycin.
(4) Ophthalmic curative medicines such as tetracyclin, chlorotetracyclin, bacitracin, neomycin, polymycin, gramicidine, and oxytetracyclin.
(5) Steroidal contraceptives such as 19-nortestostetone and 17o-hydroxyprogestrone.

Examples of the enzymes are as follows:

Oxido-reductases: Ascorbic acid oxidase, alanine dehydrogenase, amino acid oxidase, uricase, catalase, xanthine oxidase, glucose oxidase, glucose-6-phosphoric acid dehydrogenase, glutamic acid dehydrogenase, diaphorase, cytochrome-C oxidase, tyrosinase, lactic acid dehydrogenase, malic acid dehydrogenase, peroxidase, 6-phosphogluconic acid dehydrogenase, and leucine dehydrogenase.

Transferases: Aspartic acid acetyl transferase, aspartic acid amino transferase, amino acid amino transferase, glycin amino transferase, alanine amino transferase, acetic acid kinase, adenylate kinase, creatin phosphokinase, glucokinase, hexokinase, phosphoacetyl kinase, pyruvic acid kinase, and fructokinase.

Hydrolases: Amylase, asparaginase, acetylcholine esterase, aminoacylase, alginase, invertase, urease, uricase, urokinase, esternase, kallikrein, chymotrypsin, trypsin, thrombin, naringinase, nucleotidase, papain, hyaluronidase, plasmin, pectinase, hesperidinase, pepsin, penicillinase, penicillin amidase, phospholipase, phosphatase, lactase, lipase, ribonuclease, rennin, and dehalogenases.

Lyases: Aspartic acid decaboxylase, aspartase, citric acid lyase, glutamic acid decarboxylase, threonine aldolase, hystidine ammonia lyase, phenylalanine ammonia lyase, fumarase, fumaric acid hydrase, malic acid synthetase, and methioninase.

Isomerases: Alanine raceace, glucose isomerase, glucose phosphate isomerase, glutamic acid raceace, lactic acid raceace, methionine raseace, and superoxide dismutase.

Ligases: Amino acid activating enzyme, asparagin synthetase, glutathione synthetase, glutamin synthetase, and pyruvic acid synthetase.

The solvent used for dissolving such a drug is selected from among known solvents for particular drug. Examples of typical solvents advantageously used for this purpose include water, alcohols such as methyl alcohol, ethyl alcohol, propyl alcohol, and butyl alcohol, and ketones such as acetone. The concentration of the drug to be dissolved in such a solvent is determined by the amount of the drug desired to be contained in the donor. Generally, this concentration is desired not to exceed 20% by weight, and preferred falls in the range of from 0.5 to 10% by weight, based on the total weight of the solution. The liquid coagulant contained in the swelled mass and the solvent for the drug are preferably substances of different kinds, although even when they happen to be the same, the donor of this invention can be obtained satisfactorily.

The impregnation of the swelled mass with the solution containing the drug is advantageously effected by keeping the swelled mass immersed in the solution containing the drug until the liquid coagulant in the swelled mass is displaced by the solution containing the drug. The duration of the immersion of the swelled mass in the solution containing the drug must be sufficient for the solution of the drug to infiltrate the swelled mass thoroughly. It, therefore, depends on the size of the swelled mass. The duration is long when the swelled mass has a large thickness. It is short when the swelled mass is in the form of fine fibers. Generally, this duration is desired to be not less than 30 minutes, desirably not less than two hours, and more desirably not less than 12 hours. The temperature of the immersion is not more than 40° C. because most drugs are deactivated at elevated temperatures. There are drugs which require the immersion to be carried out at lower temperatures, e.g., not exceeding 10° C.; this is determined based on the known properties of each particular drug.

By the method of this invention, a donor containing a drug in the amount of 50% by weight based on the weight of the chitin can be prepared.

The factors which determine the concentration of the drug contained in the donor are the degree of swelling of the chitin-containing swelled mass (volume of swelled mass/volume of dried mass) and the concentration of the solution containing the drug. A donor containing a drug in a high concentration, therefore, can be obtained by heightening the degree of swelling or increasing the concentration of the drug. The degree of swelling depends on the concentration of the chitin dope. As a general trend, the swelled mass obtained from a dope of low concentration has a high degree of swelling and that from a dope of high concentration has a low degree of swelling. When the dope to be used has a concentration in the range of 0.2 to 10% by weight, the produced swelled mass may possess a degree of swelling in the range of 1.5 to 150, for example. For the purpose of this invention, the degree of swelling is preferably desired to fall in the range of 3 to 80. The swelled mass may be dried either by standing under normal pressure, or by standing under a vacuum. The drying is desired to be carried out at a low temperature not exceeding 10° C.

The shape of the finished donor results from natural contraction of the shape of the swelled mass. By selecting the shape of the swelled mass, therefore, the donor of a desired volume in any desired shape such as, for example, a cylinder, a semicylinder, a ring, or a hexagon can be produced. The volume of the donor and the amount of the drug are variable depending on the region of a living body at which the donor is intended to be put to use, the kind of drug, and the time intended for administration of the drug. That is, they are designed depending on the particular nature of the use of the donor. They are particularly variable with the activity of the drug to be used. By suitably adjusting all these factors, therefore, the amount of release of the drug and the duration of release can be controlled with in wide ranges. The shape of the donor is designed in due consideration of the region of the living body at which the donor is to be put to use. In any event, the donor is not desired to possess sharp corners which are liable to irritate or otherwise stimulate the internal tissue of the living body. The donor may have its shape varied without altering the dose of the drug contained therein. The original shape in which the donor is obtained, therefore, has no decisive significance. The size of the donor may be varied in a wide range. The lower limit of the size of the donor is fixed by the smallest possible shape of the donor which permits the drug to be applied to the surrounding tissues in the specific dose sufficient to induce a desired pharmacological reaction.

The donor produced in a shape and size described above manifests its activity locally in the internal region requiring medication under the biological environment, and proves most desirable for the local treatment of a specific internal region. At the fixed internal region, the donor can continuously release the drug over a long period of time, such as, for example, 24 hours to three months. Thus, the donor entails no waste of the drug and involves a very slight secondary effect. In accordance with this invention, the drug can be contained in the donor during the course of the manufacture of the shaped swelled mass involving the steps of immersing the swelled mass prepared from the chitin dope in the solution containing the drug and drying the wet swelled mass. This invention, therefore, can be applied advantageously to commercial product of a drug donor.

In the following, the present invention is illustrated in greater detail by examples. However this invention is not limited to these examples.

EXAMPLE 1

Chitin powder (made by Kyowa Oils and Fats) was comminuted to 100 mesh, treated with 1 N HCl at 4° C. for one hour, heated in 3% NaOH solution at 90° to 100° C. for three hours to remove calcium and proteins from the chitin powder, washed repeatedly in water, and dried.

The chitin thus purified was dissolved in a concentration of 5% by weight in a mixed solvent of dimethylacetamide with lithium chloride of 7% by weight at room temperature. The highly viscous transparent liquid thus obtained was filtered under pressure through a stainless steel net of 1480 mesh and stirred under a vacuum to defoam.

The resultant solution was placed in a tank, transported by a gear pump under pressure, extruded through a circular die 12 mm in diameter into acetone, left standing therein for 24 hours to coagulate. Consequently, a swelled cylinder of 10 mm in diameter was produced. This swelled cylinder was cut to lengths of 15 mm to obtain multiple cylinders. These cylinders were again washed with acetone until the solvent was thoroughly removed. The swelled masses were kept immersed in an aqueous solution containing 10 mg of Bleomycin per ml at 4° C. for 24 hours. After the immersion, the swelled masses were vacuum dried at 10° C. for 10 hours. As the result, there were obtained cylinders 3 mm in diameter and 4 mm in length.

Ten such cylinders were thoroughly sterilized by ethylene oxide gas of 1 kg/cm$^2$ pressure at 40° C. and embedded one each in the axillary region of each of 10 ICR type female mice in which tumors had been grown in advance by hypodermic transplantation of $2 \times 10^6$ cells/mouse of Sarcom 180 in the axillary region. For comparison, 10 other ICR type female mice in which tumors had been grown in advance similarly were given an intra-abdominal injection of Bleomycin at a dosage of 1 mg/day.

As the result, in the group of mice which received the intraabdominal injection, such symptoms of poisoning as piloerection and atrophy were observed. During the period of 5th through 15th days, seven out of ten mice died. On the 22nd day, the remaining three mice also died. In the group of mice which had donors of this invention embedded in the bodies, one mouse died on the 24th day and the remaining nine mice were still surviving on the 40th day. After the elapse of 40 days, the surviving mice were sacrificed, and the regions containing the embedded donors were visually examined. The donors were found to contain numerous cracks, indicating that the assimulation of the drug by the surrounding tissues had progressed.

EXAMPLE 2

The same dope as prepared in Example 1 was extruded through a circular die 8 mm in diameter into ethanol and left standing therein for 24 hours to coagulate therein. Consequently, a swelled cylinder 15 mm in diameter was obtained.

This swelled cylinder was cut to lengths of 20 mm to obtain multiple cylinders. These cylinders were washed with ethanol until the solvent was thoroughly removed. Then, the cylinders were kept immersed in an aqueous solution containing 10 mg of mitomycin C per ml at 5° C. for 24 hours. After the standing, the cylinders were removed from the solution and vacuum dried at 5° C. for 24 hours. Consequently, there were obtained cylinders 4 mm in diameter and 6 mm in length. The cylinders were placed in physiological saline solution (at 37° C.) and the saline water was sampled and assayed for mitomycin C content at stated intervals by means of a spectroscope. The time-course change in the amount of the antibiotic released from the donor into the saline solution was found as shown in Table 1.

Table-1

| Number of days | Total amount of mitomycin C (mg) |
| --- | --- |
| 1 | 3.22 |
| 3 | 6.10 |
| 5 | 8.91 |
| 10 | 10.1 |
| 15 | 12.2 |

It is noted from Table 1 that gradual release of mitomycin C from the donor was still continuing after elapse of 15 days, indicating that the donor behaved advantageously in the prolonged release of drug.

EXAMPLE 3

The same chitin powder as prepared in Example 1 was dissolved in a concentration of 2% by weight in a mixed solvent of N-methyl pyrrolidone and lithium chloride at room temperature. The highly viscous transparent solution consequently formed was filtered under pressure through a stainless steel net of 1480 mesh and defoamed by stirring under a vacuum. The resultant solution was introduced in a tank, transported under pressure by a gear pump, and extruded through a spinning nozzle containing 150 orifices 0.07 mm in diameter into methanol to be coagulated therein. Consequently, a cotton-like mass of fine fibers was obtained. This mass was washed with fresh methanol until the solvent was thoroughly removed. The swelled fibers had an outside diameter of about 120 $\mu$m. A 535-mg portion of the mass of fibers, in their swelled state or the state still containing methanol therein, was immediately immersed in a 10 mM phosphate buffer solution containing 5000 units of lipase per ml at 4° C. and left standing therein for 24 hours. After the standing, the portion was vacuum dried at 10° C. After the drying, it weighed 52 mg. This cotton-like portion was tested for lipase activity by the following procedure. First, 25 v/v% of olive oil and 2% PVC were treated with ultrasonic treatment for 20 seconds to produce an emulsion. In 5 ml of this emulsion, 5 ml of 50 mM phosphate buffer (pH=7.8) and the cotton-like portion were treated at 37° C. for one hour and then mixed with 10 ml of acetone. Then, the solution was adjusted to a pH of 9.0 by dropwise addition of 0.05 N NaOH solution. The amount of the NaOH solution required for this pH adjustment was 2.1 ml. Separately, lipase having 2500 units of activity was combined with 5 ml of the aforementioned olive oil emulsion and 5 ml of 50 mM phosphate buffer (pH=7.8) and tested for NaOH solution consumption by following the same procedure. In this case, the amount of the NaOH solution was 2.4 ml. These results indicate that the method of this invention can retain lipase within the chitin without any sacrifice of the activity.

EXAMPLE 4

The same chitin powder as prepared in Example 1 was dissolved in a concentration of 0.8% by weight in a mixed solvent of N-methyl pyrrolidone and lithium chloride at room temperature. The transparent solution consequently obtained was placed in a tube of 5 mm inside diameter and extruded through a die into methanol as a liquid coagulant. Thus, there were obtained a total of 20 extruded cylinders 1 cm in length. The cylinders were washed repeatedly with methanol until the N-methyl pyrrolidone and lithium chloride contained therein were thoroughly removed. At the end of the washing, the cylinders were 5.6 mm in outside diameter and 1.1 cm in length. The cylinders were treated with distilled water to displace the methanol and were then kept immersed in an aqueous solution containing 1% by weight of trypsin at 5° C. for 24 hours. The swelled cylinders were vacuum dried at 10° C. for 24 hours to remove water. After the drying, the 20 donors weighed 32 mg. Further, the donors were immersed in water and treated in an autoclave under 1.1 kg/cm$^2$ of pressure at 120° C. for three hours to expel trypsin. After this treatment, they were washed and dried and weighed. At this time, the weight was 24 mg, indicating that the donor still contained about 25% by weight of trypsin.

While the invention has been described in detail and with reference to specific embodiments thereof, it will be apparent to one skilled in the art that various changes and modifications can be made therein without departing from the spirit and scope thereof.

What is claimed is:

1. A method for the manufacture of a biodegradable drug donor capable of gradually releasing a drug to a living body, said method comprising dissolving a chitin which is a poly-(N-acetyl-D-glycosamine) or a chitin derivative selected from the group consisting of deacetylation products, etherification products, esterification products, carboxymethylation products, hydroxyethylation products and o-ethylation products of poly-(N-acetyl-D-glycosamine) in a solvent to thereby prepare a dope, bringing said dope into contact with a liquid coagulant to thereby form a swelled mass containing said chitin, impregnating said chitin-containing swelled mass with a solution containing a drug, and subsequently drying the impregnated swelled mass, and wherein the swelled mass has a degree of swelling in the range of 1.5 to 150.

2. A method as in claim 1, wherein the chitin is dissolved in a solvent selected from the group consisting of trichloroacetic acid, a mixture of trichloroacetic acid with a halogenated carbon compound, dichloroacetic acid, a mixture of dichloroacetic acid with a halogenated carbon compound, a mixture of N-methylpyrrolidone with lithium chloride, a mixture of dimethylacetamide with lithium chloride, trifluoroacetone, hexafluoroisopropyl alcohol, and an aqueous solution containing acetic acid.

3. A method as in claim 1, wherein the liquid coagulant is selected from the group consisting of water, an alcohol and a ketone.

4. A method as in claim 1, wherein the solvent for forming the solution containing the drug is selected from the group consisting of water, an alcohol, and a ketone.

5. A method as in claim 1, said method comprising dissolving a chitin in a solvent selected from the group consisting of trichloroacetic acid, a mixture of trichloroacetic acid with a halogenated carbon compound, dichloroacetic acid, a mixture of dichloroacetic acid with a halogenated carbon compound, a mixture of N-methylpyrrolidone with lithium chloride, a mixture of dimethylacetamide with lithium chloride trifluoroacetone, hexafluoroisopropyl alcohol, and an aqueous solution containing acetic acid to thereby prepare a dope, bringing said dope into contact with a liquid coagulant selected from the group consisting of water, an alcohol, and a ketone to thereby form a swelled mass containing said chitin, impregnating said chitin-containing swelled mass with a solution containing a drug and a solvent selected from the group consisting of water, an alcohol and a ketone, and subsequently drying the impregnated swelled mass.

6. A method as in claim 1, wherein the concentration of the drug in the solution for impregnating the chitin-containing swelled mass is from 0.5 to 10% by weight, based on the total weight of the solution.

7. A method as in claim 5, wherein the concentration of the drug in the solution for impregnating the chitin-containing swelled mass is from 0.5 to 10% by weight, based on the total weight of the solution.

8. A method as in claim 1, wherein the liquid coagulant and the solvent for the solution containing the drug are different.

9. A method as in claim 5, wherein the liquid coagulant and the solvent for the solution containing the drug are different.

10. A method as in claim 1, wherein the swelled mass is impregnated with the solution containing the drug by immersion of the swelled mass in the solution containing the drug until the liquid coagulant in the swelled mass is displaced by the solution containing the drug.

11. A method as in claim 5, wherein the swelled mass is impregnated with the solution containing the drug by immersion of the swelled mass in the solution containing the drug until the liquid coagulant in the swelled mass is displaced by the solution containing the drug.

12. A method as in claim 8, wherein the swelled mass is impregnated with the solution containing the drug by immersion of the swelled mass in the solution containing the drug until the liquid coagulant in the swelled mass is displaced by the solution containing the drug.

13. A method as in claim 9, wherein the swelled mass is impregnated with the solution containing the drug by immersion of the swelled mass in the solution containing the drug until the liquid coagulant in the swelled mass is displaced by the solution containing the drug.

14. A biodegradable drug donor capable of gradually releasing a drug to a living body manufactured by a method comprising dissolving a chitin which is a poly-(N-acetyl-D-glycosamine) or a chitin derivative selected from the group consisting of deacetylation products, etherification products, esterfication products, carboxymethylation products, hydroxyethylation products and o-ethylation products of poly-(N-acetyl-D-glycosamine) in a solvent to thereby prepare a dope, bringing said dope into contact with a liquid coagulant to thereby form a swelled mass containing said chitin, impregnating said chitin-containing swelled mass with a solution containing a drug, and subsequently drying the impregnated swelled mass, and wherein the swelled mass has a degree of swelling in the range of 1.5 to 150.

15. A biodegradable drug donor as in claim 14, wherein the chitin is dissolved in a solvent selected from the group consisting of trichloroacetic acid, a mixture of trichloroacetic acid with a halogenated carbon compound, dichloroacetic acid, a mixture of dichloroacetic acid with a halogenated carbon compound, a mixture of N-methyl-pyrrolidone with lithium chloride, a mixture of dimethylacetamide with lithium chloride, trifluoroacetone, hexafluoroisopropyl alcohol, and an aqueous solution containing acetic acid.

16. A biodegradable drug donor as in claim 14, wherein the liquid coagulant is selected from the group consisting of water, an alcohol, and a ketone.

17. A biodegradable drug donor as in claim 14, wherein the solvent for forming the solution containing the drug is selected from the group consisting of water, an alcohol, and a ketone.

18. A biodegradable drug donor as in claim 14 manufactured by a method comprising dissolving a chitin in a solvent selected from the group consisting of trichloroacetic acid, a mixture of trichloroacetic acid with a halogenated carbon compound, dichloroacetic acid, a mixture of dichloroacetic acid with a halogenated carbon compound, a mixture of N-methylpyrrolidone with lithium chloride, a mixture of dimethylacetamide with lithium chloride, trifluoroacetone, hexafluoroisopropyl alcohol, and an aqueous solution containing acetic acid to thereby prepare a dope, bringing said dope into contact with a liquid coagulant selected from the group consisting of water, an alcohol, and a ketone to thereby form a swelled mass containing said chitin, impregnating said chitin-containing swelled mass with a solution containing a drug and a solvent selected from the group consisting of water, an alcohol, and a ketone, and subsequently drying the impregnated swelled mass.

19. A method as in claim 1, wherein said dope has a chitin concentration in the range of from 0.2 to 10% by weight.

20. A biodegradable drug donor as in claim 14, wherein said dope has a chitin concentration in the range of from 0.2 to 10% by weight.

21. A method as in claim 1, wherein said drug is selected from the group consisting of a proteinaceous medicine, an antibiotic, a cancer depressant, a steroidal contraceptive and an enzyme.

22. A biodegradable drug donor as in claim 14, wherein said drug is selected from the group consisting of a proteinaceous medicine, an antibiotic, a cancer depressant, a steroidal contraceptive and an enzyme.

23. A method as in claim 2, wherein said solvent is selected from the group consisting of the mixture of trichloroacetic acid with a halogenated carbon compound in a weight ratio of 20/80 to 80/20, the mixture of dichloroacetic acid with a halogenated carbon compound in a weight ratio of 20/80 to 80/20, the mixture of N-methylpyrrolidone with lithium chloride in a weight ratio of 90/10 to 95/5 and the mixture of dimethylacetamide with lithium chloride in a weight ratio of 90/10 to 95/5.

24. A biodegradable drug donor as in claim 15, wherein said solvent is selected from the group consisting of the mixture of trichloroacetic acid with a halogenated carbon compound in a weight ratio of 20/80 to 80/20, the mixture of dichloroacetic acid with a halogenated carbon compound in a weight ratio of 20/80 to 80/20, the mixture of N-methylpyrrolidone with lithium chloride in a weight ratio of 90/10 to 95/5 and the mixture of dimethylacetamide with lithium chloride in a weight ratio of 90/10 to 95/5.

* * * * *